(12) United States Patent
Garner

(10) Patent No.: US 11,484,444 B1
(45) Date of Patent: Nov. 1, 2022

(54) COOL COMPRESSION STOCKINGS

(71) Applicant: Carols LLC, Mason, OH (US)

(72) Inventor: Carol Garner, Mason, OH (US)

( * ) Notice: Subject to any disclaimer, the term of this patent is extended or adjusted under 35 U.S.C. 154(b) by 390 days.

(21) Appl. No.: 14/953,418

(22) Filed: Nov. 29, 2015

Related U.S. Application Data

(60) Provisional application No. 62/123,824, filed on Dec. 1, 2014.

(51) Int. Cl.
*A61F 13/08* (2006.01)
*A61F 13/00* (2006.01)

(52) U.S. Cl.
CPC ........ *A61F 13/08* (2013.01); *A61F 13/00063* (2013.01); *A61F 13/00995* (2013.01)

(58) Field of Classification Search
CPC ............... A61F 13/08; A61F 13/00063; A61F 13/00995; A61F 13/061; A61F 13/107; A61F 5/0109; A61F 13/10; A41B 11/00; A41B 17/00
See application file for complete search history.

(56) References Cited

U.S. PATENT DOCUMENTS

| | | | | |
|---|---|---|---|---|
| 2,901,901 A | * | 9/1959 | Baker ..................... | A41B 11/00 66/172 E |
| 3,443,404 A | * | 5/1969 | Knohl ..................... | D04B 1/18 66/178 A |
| 3,900,035 A | * | 8/1975 | Welch ..................... | A61F 7/10 607/108 |
| 4,397,161 A | | 8/1983 | Cheesebro, Jr. et al. | |
| 4,561,267 A | | 12/1985 | Wilkinson et al. | |
| D397,863 S | | 9/1998 | Van De Steeg | |
| 5,898,948 A | | 5/1999 | Kelly et al. | |
| 6,012,177 A | | 1/2000 | Cortinovis | |
| 6,032,296 A | | 5/2000 | Kelly et al. | |
| 6,331,334 B1 | | 11/2001 | Reinhardt et al. | |
| 6,610,084 B1 | | 8/2003 | Torres | |
| 6,725,691 B2 | | 4/2004 | Yakopson | |
| 7,441,419 B1 | | 10/2008 | Dollyhite et al. | |
| 9,062,913 B2 | | 6/2015 | Aranjo et al. | |
| 9,724,260 B2 | * | 8/2017 | Winkler, Sr. ............ | A61F 13/08 |
| 2008/0249454 A1 | * | 10/2008 | Mills ....................... | A61F 13/08 602/63 |
| 2010/0137776 A1 | | 6/2010 | Virkus | |

(Continued)

FOREIGN PATENT DOCUMENTS

CN 202107930 U 3/2015

OTHER PUBLICATIONS

Zensah Women's Athletic Socks, most recently viewed at http://www.zensah.com/women/women-leg-sleeves/compression-leg-sleeves.html, Nov. 22, 2015.

(Continued)

*Primary Examiner* — Ophelia A Hawthorne
(74) *Attorney, Agent, or Firm* — Law Office of Fran Sweeney LLC

(57) ABSTRACT

Cool Compression Stockings are three-in-one stockings that address needs both in the sports world and the medical field. The stockings have an outer layer with compression points and a plurality of alternating strips spaced apart from each other, configured to accommodate cold packs. The inner layer contains antimicrobial properties that help suppress the occurrence of bacteria.

1 Claim, 4 Drawing Sheets

(56) References Cited

U.S. PATENT DOCUMENTS

| | | | |
|---|---|---|---|
| 2011/0214315 A1* | 9/2011 | Mayer | A61F 5/14 36/140 |
| 2013/0133353 A1* | 5/2013 | Araujo | F25D 31/00 62/331 |
| 2013/0172926 A1* | 7/2013 | Barker | A61F 13/08 606/201 |
| 2014/0024990 A1* | 1/2014 | Valois | A61F 13/08 602/62 |

OTHER PUBLICATIONS

Dr. Scholls compression socks, most recently viewed at http://www.compressionsale.com/dr-scholls-socks/, Nov. 22, 2015.
Bright Life Compression Stockings, most recently viewed at http://www.brightlifedirect.com/COMPRESSION-LEVEL.asp, Nov. 22, 2015.
CJ Moffatt, Compression Hosiery in Lymphoedema, BSN Medical, MEP LTD. 2006, last viewed at http://www.lympho.org/mod_turbolead/upload/file/Lympho/Template_for_Practice_-_Compression_hosiery.pdf, Nov. 21, 2015.
http://www.compressionsale.com/juzo/?gclid=CP7n88KWt8kCFcQkgQodTAcOug, Nov. 29, 2015.
https://www.ameswalker.com/prodcat/womens-compression-socks.asp, Nov. 29, 2015.
http://www.compressionstore.com/compression-socks/pc/Sigvaris-Women-c239.htm, Nov. 29, 2015.
http://www.compressionsale.com/therafirm?gclid=CO3Ineaat8kCFdcZgQodF0oCcg, Nov. 29, 2015.
http://www.foryourlegs.com/welcome-jobst-p-1-c-753.html?gclid=CKy4nfCbt8kCFUg7gQodYBEOjw, Nov. 29, 2015.

\* cited by examiner

COOL COMPRESSION STOCKINGS

CROSS-REFERENCE TO RELATED APPLICATIONS

This application claimes the benefit of U.S. Provisional Application number 62/123,824, filed Dec. 1, 2014, having the title "Cool Compression Stockings," by Carol Garner, which is incorporated herein by reference in its entirety.

FIELD OF DISCLOSURE

The present invention disclosure relates to compression stockings that relieve a number of uncomfortable conditions that can arise when participating in sports events or during ordinary daily activities for individuals with medical ailments.

BACKGROUND

Compression stockings and orthopedic stockings, particularly when worn to treat medical conditions, are not designed with appearance in mind. Traditionally compression stockings are unattractive, thus causing embarrassment for those required to wear them. Compression stockings that provide a cooling effect to the user's leg are beneficial for both sports enthusiasts and for those with circulation disorders. Compression stockings made from a fabric with an antimicrobial particle may reduce odor caused from excessive perspiration generated during sports activities. Compression stockings made from a fabric with an antimicrobial particle may also reduce the incidence of bacterial infections that could arise when users with compromised skin conditions are required to wear compression stockings around the clock for health reasons.

BRIEF SUMMARY OF THE INVENTION

One embodiment of the invention features a compression stocking with a cooling fabric embedded with antimicrobial particles. Cool compression stockings exert pressure along a foot surface and lower leg surface to provide support and enhance circulation. A cooling component in the compression stocking's fabric produces a cooling effect when the fabric is in contact with skin. When compression stockings also feature fabric containing antimicrobial particles, the likelihood of bacterial growth is reduced.

DETAILED DESCRIPTION OF THE INVENTION

Figure 1:
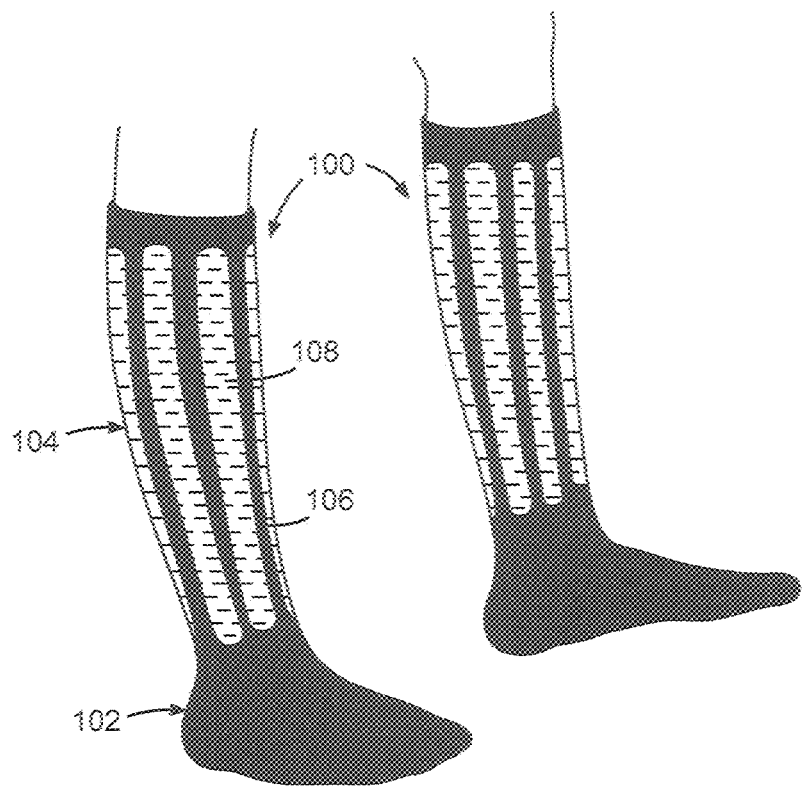
FIG. 1 shows one embodiment of cool compression stockings. In this view, the cooling strips run vertically from a neck portion of a foot to the area of a leg just below a knee.
Figure 1:
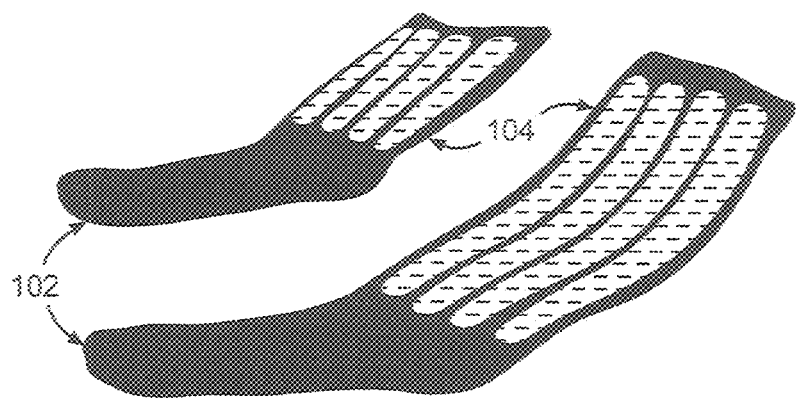

Reference is now made in detail to the description of the embodiments as illustrated in the drawings. While several embodiments are described in connection with these drawings, there is no intent to limit the disclosure to the embodiment or embodiments disclosed herein. On the contrary, the intent is to cover all alternatives, modifications, and equivalents.

Although exemplary embodiments are shown and described, it will be clear to those of ordinary skill in the art that a number of changes, modifications, or alterations to the disclosure as described may be made. An all cotton or all polyester fabric could be used in the place of the elasticized nylon cotton blend portion of the compression stocking. Cooling fabric technology is a rapidly developing field as is the technology that teaches how to infuse gold, silver or other antimicrobial agents into fabrics. One skilled in the art of compression stockings will appreciate that a number of permutations of these technologies can be added and included without altering the terms described in the claimed invention.

Currently, numerous compression stockings exist. However, these stockings suffer from various drawbacks. In many instances compression stockings worn for medical purposes are white or flesh-colored and call attention to one's impairment. The disclosed product and method provide an alternative approach that remedies the various drawbacks existent in those previously proposed products and methods.

As defined herein, the term "antimicrobial nanoparticle" refers to particles that are used for a variety of different antimicrobial applications. For example, silver compounds and silver ions have been known to show antimicrobial properties and have been used in a wide range of applications. Silver nanoparticles have an antibacterial effect, and are also used in a variety of consumer products such as workout clothing to reduce or prevent the odor that builds up when users perspire profusely.

As defined herein, the term "compression stockings" refers to specialized hosiery, designed to help prevent the occurrence of, and guard against further progression of certain medical conditions. Athletes may also wear compression stockings in order to enhance performance during sports practices and contests. Compression stockings are worn around the foot and leg, compressing the limbs. Compression stockings may also include support hose and elastic leggings. Herein, the compression fabrics selected may exert anywhere from approximately 8-15 mmHg (millimeters of mercury) up to approximately 40-50 mmHg of pressure.

As defined herein, the term "fabric" refers to the basic structure of an object, namely a textile including woven and knitted materials.

As defined herein, the term "nanoparticle" refers to particles with sizes between approximately 1 and 200 nanometers.

Compression Fabrics

Referring to FIG. 1, the compression stocking is made of an elasticized nylon-cotton blend fabric. A salient feature here is that the stocking is shown in a dark color, rather than a clinical flesh hue or hospital-white color. The dark-colored stocking in this embodiment would go unnoticed and would be acceptable attire with slacks. In another embodiment, colors other than black or white are available. Although some athletic stockings with minimal compression also feature colors and patterns, these colors and patterns are not enjoying widespread use in the medical field.

Referring again to FIG. 1, the elastic materials and threads as well as the elasticity characteristics in the stocking comply with medical compression stocking standards as outlined under RAL-GZ 387 of September 2000. The RAL-GZ 387 Standards govern quality assurance testing of medical compression stockings. These standards were initiated originally to assure best treatment practices for lymphoedema and are now enjoying widespread use when treating other medical conditions.

The compression fabric in cool compression stockings may exert a pressure on user's legs anywhere from approximately 8-15 mmHg to approximately 40-50 mmHg.

The 8-15 mmHg range is the lightest form of compression. The lightest form of compression will still energize the user's legs and offer some assistance for tired and achy legs. Enhanced blood circulation is experienced, which helps control swelling. The lightest form of compression is ideal for an athlete.

Relief from minor to moderate swelling, aching, and the occurrence of varicose veins is felt from the mild compression of 15-20 mmHg. Those who are required to sit or stand for long periods of time will see a benefit to a mild compression stocking. Compression within the 15-20 mmHg range is sufficient to help prevent deep vein thrombosis for long distance travelers.

Physicians may prescribe a moderate compression stocking where the pressure is between 20-30 mmHg. Stockings in this range of pressure treat a number of mild to moderate medical conditions including chronic varicose veins, edema, and deep vein thrombosis.

Physician supervision is typically involved with compression stockings in the 30-40 mmHg range. While providing relief from some of the same conditions as a moderate compression stocking, including chronic varicose veins, edema, and deep vein thrombosis, these stockings are also helpful in healing active venous stasis ulcers.

The 40-50 mmHg pressure is required to treat chronic venous insufficiency and post-thrombotic syndrome and other compromised medical conditions. The 40-50 mmHg compression fabric is typically used only when prescribed by a physician.

Cooling Fabrics

Those skilled in the art of cooling fabrics will recognize that cooling fabrics exist that wick perspiration from the skin at which time the skin feels cooler. Other cooling fabrics may include cooling elements coupled to a base fabric. Cooling elements may include cooling gels or polymers or phase change materials. The cooling elements may undergo a chemical or physical change when exposed to moisture, where heat is absorbed in the process.

Therapeutic cold packs at temperatures lower than the normal temperature of the human body have been used medically for centuries to help reduce pain and swelling. One skilled in the art of cold packs will recognize that cold packs that are shapeable to the contours of a leg and foot over a range of temperatures exist. Currently, the medical application of gel packs restricts the user's mobility, normally confining the user to a chair or bed during use. A shapeable therapeutic cold pack attached to a compression stocking allows a user to remain mobile during the administration of cold therapy.

Antimicrobial Properties in Compression Fabrics and Cooling Fabrics

Antimicrobials, including antimicrobial nanoparticles, may be added to fabrics to reduce the odor from excessive perspiration build-up as well as to reduce bacterial growth. In one embodiment, silver nanoparticles may be added to the cooling fabric to prevent the likelihood of infection when the compression stockings are in contact with the skin for long periods of time, or when the skin is delicate and tends to break down.

Cool Compression Stockings

Referring to FIG. 1, the cool compression stocking 100 covers the foot 102, and leg 104. In another variation, and referring to FIG. 5A, the cool compression stocking originates at the cuff 214 and terminates at a point just where the foot portion 220 begins. In yet another variation, and referring to FIG. 5B, the cool compression stocking originates at the cuff 214 and terminates at a location on top of a foot 218 at a point where the arch of the bottom of the foot 224 is at its highest point distant from the heel 204 of the foot 224.

Figure 2:
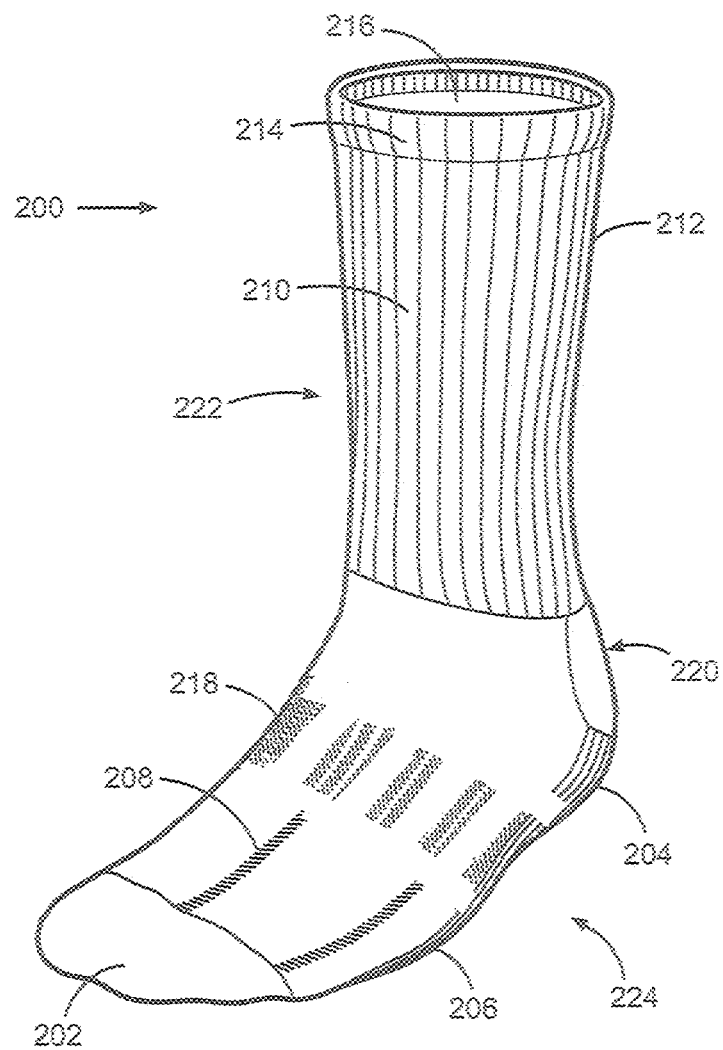
FIG. 2 shows a generic compression stocking that include cooling devices and antimicrobial particles on an inside surface of the compression fabric.

In the preferred embodiment and referring to FIG. 1, a compression fabric exerts a select range of pressures along the upper and lower portions of a user's foot 102 and the calf and shin portions of the leg 104. Referring to FIG. 2, increased pressure is applied in the preferred embodiment on the foot 224 on the heel 204, on the top portions 208, 218 and on the bottom portion 206 of the foot 224. Pressure is applied over all portions of the leg 222. Illustrative of the pressure points on the leg 222 are pressure points on the shin 210 and calf 212 portions of the leg.

In the preferred embodiment, and referring to FIG. 1, the compression fabric 106 and the cooling fabric 108 are shown in contrasting colors. One such cooling fabric is a polyvinyl alcohol fabric and those skilled in the art of cooling fabrics will recognize that there are numerous variations of cooling fabrics currently in the marketplace.

Figure 3:
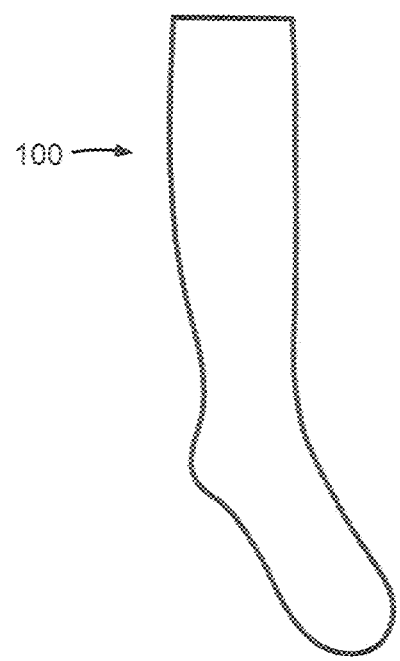
FIG. 3 shows a side view of a compression stocking before modifications are made to add cooling fabric.
Figure 4:
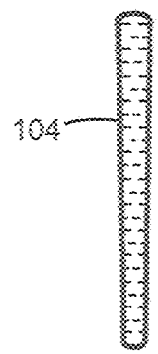
FIG. 4 shows an example of a cooling fabric before it is incorporated into the body of the stocking.

In order to assemble the cool compression stocking in the preferred embodiment, and referring to FIG. 3, one begins with a compression fabric 100 shown in FIG. 3 in white. The compression fabric is adapted to receive strips of a cooling fabric 104. For illustrative purposes the cooling fabric 104 is shown in a second color. During manufacture, the compression fabric and cooling fabric may be knitted together in alternating strips or operatively connected in strips to create the cool compression stocking as shown in FIG. 1. Although in FIG. 3 the stocking 100 and cooling fabric 104 are shown in contrasting colors, in another embodiment, the stocking 100 and fabric 104 may be made with the same color.

Figure 5A:
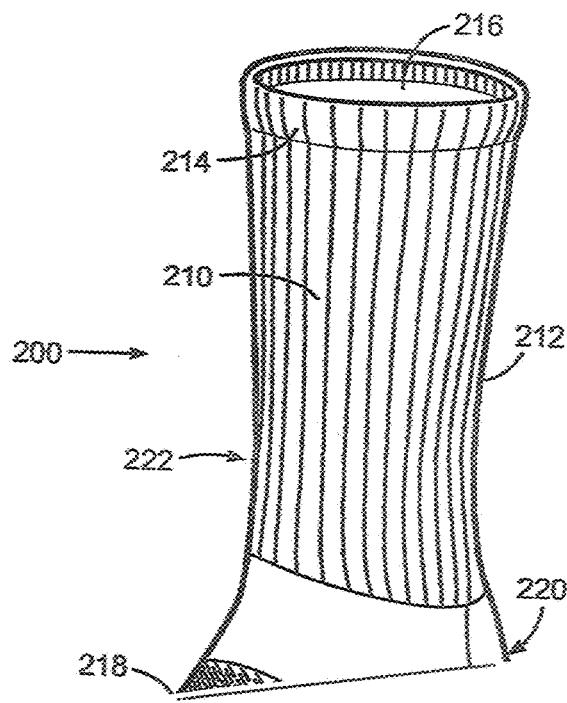
FIG. 5A shows an example of a cool compression stocking that originates at a point just below a knee and terminates at an ankle.
Figure 5B:
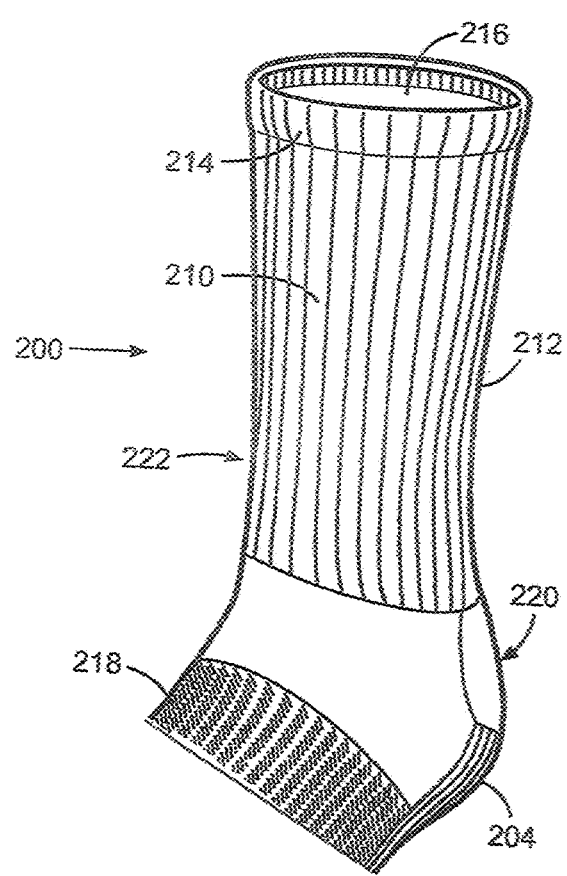
FIG. 5B shows an example of a cool compression stocking that originates at a point just below a knee and terminates at a mid-point of a foot.

In a variation of the preferred embodiment, the cooling fabric may originate at the cuff 214 of the stocking and terminate at any point in the leg area 222 or at any point in the foot area 224 of the stocking up to and including the toe 202 portions. The style of the cools compression stocking may be modified for comfort or to allow easy access for medical procedures to the foot, as seen in FIG. 5A and FIG. 5B.

The cooling fabric 104 may also be infused with an antimicrobial particle, including a nanoparticle. Antimicrobial nanoparticles currently used include metal salts of silver, gold, zinc and titanium, but this list is not limited to silver, gold, zinc and titanium as it also may include other antimicrobial agents. Of the four metals disclosed herein and currently used, silver is currently the most widely used.

In an alternative form of the preferred embodiment, the cooling fabric is actually a fabric that encases cold packs. This cooling fabric is operatively joined to the outside layer of the compression fabric in alternating strips as shown in FIG. 1. The stockings are placed in a refrigerator or freezer until the cold packs reach a clinically designated temperature. Thereafter, the cool compression stockings in this embodiment are worn until the cooling properties of the cold packs are exhausted.

Two-Layer Cool Compression Stockings

In another embodiment, a cool compression stocking is shown as a two-layer stocking. In FIG. 2 an outside surface of the compression fabric is defined by a toe portion 202, a heel portion 204, a top surface 208 of a foot portion and a bottom surface 206 of a foot portion, a heel portion 204, a leg portion showing a calf portion 212 and a shin portion 210, a neck portion 218, a cuff portion 214 and an inside surface 216. The stocking 100 exerts pressure on various portions of a user's foot 202, 204, 206, 208 and leg 212. The shaded areas in FIG. 2 show one embodiment wherein extra pressure is applied to the shaded areas through tightening the elasticity of the fabric in those shaded areas in compliance with RAL-GZ 387 Standards.

In the two-layer embodiment with a compression fabric as the outside layer, the inside surface 216 of the compression fabric operatively receives a cooling fabric. The cooling fabric 104 overlays the inside layer 216 of the compression fabric and is disposed onto the compression fabric in order to construct the stocking. The cooling fabric 104 may also be infused with an antimicrobial particle, including a nanoparticle. Antimicrobial nanoparticles currently used include metal salts of silver, gold, zinc and titanium, but this list is not limited to silver, gold, zinc and titanium as it also may include other antimicrobial agents. Of the four metals disclosed herein and currently used, silver is currently the most widely used.

FEATURES AND BENEFITS OF THE INVENTION

The compression component of cool compression stockings provides leg support during exertion and improves circulation. Particularly for those who reside in warmer climates and need to wear compression stockings for health reasons, the cooling feature will ensure a more comfortable experience. The addition of antimicrobial particles helps prevent infections for those whose systems may be immune-compromised or who may have difficulties removing the stockings periodically to allow the skin to breathe. This feature becomes essential for those who are required to wear compression stocking for long periods of time.

The cool compression stocking is modified to accommodate a wide range of needs. For example, after a sprain, medical procedure or surgery, an individual may prefer a compression stocking that terminates above the toes or ankle.

Athletes in a number of sports including football, baseball and soccer are required to wear knee-length hose. When athletes compete, especially in warm climates, the cooling effects of cool compression stockings, together with the antimicrobial features, will provide more comfort from heat build-up and also reduce odor-forming bacteria due to excess perspiration.

What is claimed is:
1. A cool compression stocking comprising:
a foot portion, a toe portion, a heel portion, a leg portion, a neck portion, wherein the neck portion connects the foot portion to the leg portion, and a cuff portion, wherein the cuff portion is configured to be located at a terminal point of the leg portion.
a first fabric and a second fabric wherein the first fabric comprises an outside surface wherein the outside surface exerts a compressive force on the user's foot and leg in the range of between approximately eight millimeters of mercury up to approximately fifty millimeters of mercury, and the second fabric comprises an inside surface, wherein the inside surface is comprised of antimicrobial nanoparticles, wherein the antimicrobial nanoparticles are further comprised of silver, gold, zinc, titanium or other antimicrobial agents, and the second fabric further comprises cooling elements, wherein the first fabric and the second fabric are connected in alternating strips creating a plurality of alternating strips, wherein the plurality of alternating strips are spaced apart from each other, are parallel to each other and run longitudinally from a first end of the leg area to a second end of the leg area of the compression' stocking.

* * * * *